United States Patent

[19]

Mishima

[11] Patent Number: 5,993,835
[45] Date of Patent: Nov. 30, 1999

US005993835A

[54] SKIN-WHITENING AGENT

[76] Inventor: Yutaka Mishima, 4-32,1-chome, Sowa-cho, Nada-ku, Kobe-shi, Hyogo, Japan

[21] Appl. No.: 09/059,179

[22] Filed: Apr. 14, 1998

[30] Foreign Application Priority Data

Apr. 30, 1997 [JP] Japan ................................. 9-112933

[51] Int. Cl.⁶ ............................. A61K 6/00; A61K 7/00; A61K 33/22; A01N 59/14
[52] U.S. Cl. ............................................ 424/401; 424/62
[58] Field of Search ........................ 424/401, 62, 450, 424/195.1, 657

[56] References Cited

U.S. PATENT DOCUMENTS 5,116,980  5/1992  Gabel ..................................... 544/229
5,587,173  12/1996  Junino et al. .......................... 424/401

FOREIGN PATENT DOCUMENTS 0191214  8/1986  European Pat. Off. .
512654   1/1921  France .
3203774  8/1983  Germany .
13227    5/1915  United Kingdom .

OTHER PUBLICATIONS

Inhibitory Effects of Melanin Monomers, Dihydroxyindole–2–Carboxylic Acid (DHICA) and Dihydroxyindole (DHI) On Mammalian Tyrosinase, With a Special Reference to the Role of DHICA/DHI Ratio in Melanogenesis.

Mishima A. et al., "Regulatory Factors For Polymerization Of Melanin Monomers Within Coated Vesicles And Premelanosomes In Melanoma Cells," *Melanoma Research*, 3:255–262 (1993).

Abstract of Mishima et al., "Overview of Research and Development of New Third–Generation Skin–Lighting Agents." *Fragrance J.*, 26–1:34–44 (1998).

*Primary Examiner*—Thurman K. Page
*Assistant Examiner*—Sharon Howard
*Attorney, Agent, or Firm*—Browdy and Neimark

[57] ABSTRACT

Disclosed is a skin-whitening agent which comprises as its effective ingredient a group of substances capable of forming chemical complexes with melanin monomers. Boron-containing compounds and organelles originated from animals, plants and microorganisms make the invention feasible as they commonly suppress pigmentation through a novel action mechanism where melanin monomers are trapped by chemical complex formation.

4 Claims, No Drawings

SKIN-WHITENING AGENT

BACKGROUND OF THE INVENTION

1. Field of the Invention

The present invention relates to an entirely novel type of skin-whitening agent which suppresses melanin polymer formation through trapping of melanin monomers, in particular, to a skin-whitening agent characterized in that it comprises as its effective ingredient a group of substances which bear the property of forming chemical complexes with melanin monomers.

2. Description of Prior Art

Various researches have been carried out for skin-whitening agents which may eliminate pigmented spots on human skin such as melasma and freckles, as well as enhancing throughout the whole skin the ability of retaining both beauty and whiteness. It is said that several factors such as melanin, carotene, blood stream level, skin thickness and skin transparency are involved in the color tone of healthy human skin. Among these factors, the level of eumelanin and pheomelanin are also known to be a major cause of pigmentation. Researches for skin-whitening cosmetics have also long been carried out: Such cosmetics are directed at suppressing the formation of melanin, a cause of melasma and freckles, as well as to enhance throughout the whole skin the ability of retaining both beauty and whiteness.

Recently, as to the process of forming melanin polymer in animal and human, in addition to the conventionally known pathway wherein tyrosinase participates, the presence and role of further critical pathways after DOPAchrome and their regulating enzymes are currently being clarified: Such pathways are those which proceed via two distinct types of melanin monomers, i.e. DHICA (5,6-dihydroxyindole-2-carboxylic acid) and DHI (dihydroxy-indole), while these two melanin monomers regulating enzymes are those including DOPAchrome tautomerase and DHICA-oxidase.

Various tyrosinase inhibitory compounds including kojic acid have been used as a means of suppressing the formation of melanin: Such compounds however have the disadvantage of being unsatisfactory in efficacy or lacking rapid effectiveness. Thus, there have been great expectations for the development of skin-whitening agents which are capable of achieving consistently high efficacy through any novel action mechanisms.

SUMMARY OF THE INVENTION

In view of the foregoing, the object of the present invention is to provide an entirely novel type of skin-whitening agent which bears any action mechanism different to those hitherto known.

The present inventor first directed his attention to the fact that one of the chemicals, i.e. boronophenylalanine (abbreviated "BPA" hereinafter), as tested in neutron capture therapy, previously established by the inventor as an effective therapy for malignant melanoma, specifically accumulated in melanoma cells.

On the basis of this evidence, the present inventor then energetically pursued investigations, resulting in the discovery of an entirely novel action mechanism where a series of boron-containing compounds including BPA and natural substances from organelles including CV (coated vesicles) form chemical complexes in cells with melanin monomers such as DHICA, DHI and DOPA and suppress the formation of melanin polymers in pigment cells to reduce pigmentation. The present invention was completed on the basis of these findings.

In particular, the present invention provides a skin-whitening agent characterized in that it comprises as its effective ingredient a group of substances which form chemical complexes with melanin monomers and trap them from the pathway of melanin polymer synthesis.

Further, the present invention provides a skin-whitening agent of the same type, wherein the group of substances are boron-containing compounds and/or natural substances originated from animals, plants and microorganisms.

Still further, the present invention provides a skin-whitening agent of the same type, wherein the boron-containing compound is one or more members selected from the group consisting of but not limited to boronophenylalanine, boroglycine, borodimethylglycine, potassium borotartrate, boric acid, dihydroxyphenylborane, borobetaine and tetrasodium borate.

Still further, the present invention provides a skin-whitening agent of the same type, wherein the natural substances are extracts of CV, melanosomes, lysosomes and/or other organelles originated from animals, plants and microorganisms.

DETAILED DESCRIPTION OF THE INVENTION

The formation mechanism for chemical complexes of the above described effective ingredients and melanin monomers, clarified by the present inventor, will be illustrated below using BPA as an example.

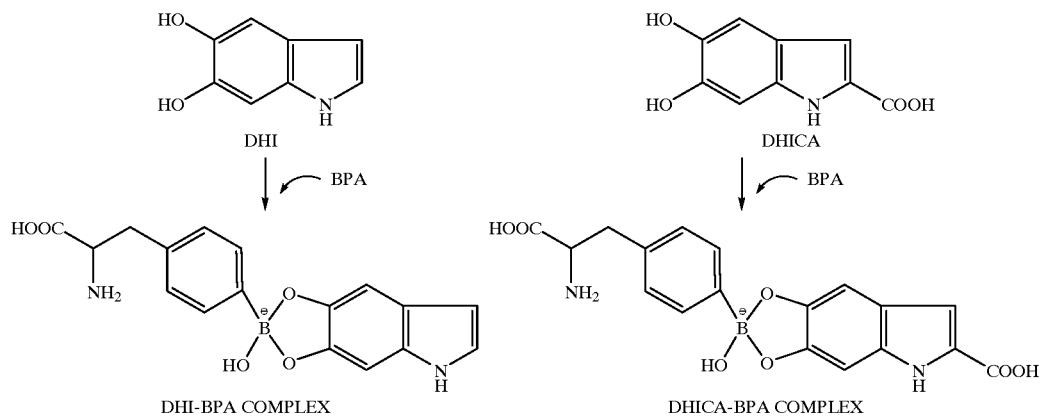

Examples of boron-containing compounds which are favorably incorporated as effective ingredients according to the present invention are one or more of the following: boronophenylalanine, boroglycine, borodimethylglycine, potassium borotartrate, boric acid, dihydroxy-phenylborane, borobetaine and tetrasodium borate.

Examples of natural substances originated from animals, plants and microorganisms are melanosomes as organelles, such as melanosomes, CV, lysosomes and organelle extracts thereof, which are prepared by the method as reported by Wilczck and Mishima (*Melanoma Res* 3:255–262,1993).

There are provided no special restrictions as to forms of the skin-whitening agent according to the present invention, as long as they are acceptable for external use: The skin-whitening agent according to the present invention is provided in extensive uses in conventional forms acceptable in pharmaceuticals and cosmetics, for example, poultice, plaster, paste, cream, ointment, tincture, aerosol, emulsion, lotion, milk, essence, gel, facial pack, powder, foundation, sunlight-shielding agent and bath salt.

Further, in the preparation of skin-whitening agents according to the present invention, the use of conventional skin-whitening compounds with action mechanisms different from that of the effective ingredient according to the present invention, in particular, ascorbic acid, arbutin and kojic acid, results in a remarkable dual effect which arithmetically or synergistically enhances the skin-whitening effect in the skin-whitening agent according to the present invention to render it very efficacious to intractable pigmentations.

In addition to these skin-whitening compounds, a variety of conventional effective ingredients, for example, peripheral vasodilators such as cepharanthine, vitamin E, vitamin E nicotinate, nicotinic acid, nicotinic acid amide, benzyl nicotinate, ginger tincture and mentha tincture, refrigerants such as camphor, menthol and mentha oil, antiseptics such as hinokitiol, benzalkonium chloride and undecylenic acid, anti-inflammatories such as adrenal cortex hormone, ε-aminocaproic acid, lysozyme chloride, glycyrrhizin and allantoin, and a variety of extracts originated from animals, plants and microorganisms such as placental extract, glycyrrhiza extract, lithospermum root extract and lactic acid bacteria-fermented extract, can be suitably used to meet respective final uses, as long as they do not hinder the attainment of the objectives of the present invention.

Still further, in the skin-whitening agent according to the present invention, in addition to the above described conventional effective ingredients, a variety of conventional moisture-retaining agents, antiseptics, antioxidants, chelating agents, pH regulating agents, flavoring agents, coloring agents, UV-absorbents and scattering agents can be used if necessary, as long as they do not hinder the attainment of the objectives of the present invention.

EXAMPLE

The present invention will be explained hereinafter by disclosing several Experiments and Formulations. Such disclosure is however only illustrative of preferred embodiments according to the present invention, and not intended in any way to limit the scope of the present invention.

Experiment 1

Test of Inhibition on the Formation of Melanochrome from DOPAchrome (a) Method

Preparation of 5 mM DOPAchrome solution as reagent

Solution A: 10 mM DOPA

Solution B: 20 mM aqueous sodium metaperiodate solution

Equi-volumes of Solutions A and B are mixed to obtain a solution of vermilion color. The solution is prepared immediately before use.

Procedure

One milliliter aliquots of 1,000 mM phosphate buffer were mixed first with either boronophenylalanine, potassium borotartrate, dihydroxylphenylborane, boroglycine, tetrasodium borate or boric acid to give respective concentrations given in Tables 1 to 7, then with pure water to bring the total volumes to 1.8 ml. The resultant solutions were then placed in 37° C. water bath, quickly mixed after adding 0.2 ml aliquots of a fresh 5 mM DOPAchrome, and allowed to react while stirring. After 30 minute reaction in the water bath, the absorbance of reaction mixtures were immediately measured at 500 nm, and color tone was observed macroscopically.

(b) Results

Results are shown in Tables 1 to 6. Dark melanochrome was formed and the formation of dark fine sediment was initiated after 30 minutes in reaction mixtures which had no effective ingredients according to the present invention. Conversely, reaction mixtures which contained any of the effective ingredients according to the present invention turned brown but caused no sedimentation as checked by macroscopic observation. These results indicated that the ingredients according to the present invention do suppress the formation of melanochrome in a concentration-dependent manner.

Further, similar results were obtained by measurement of absorbance at 500 nm as those found by macroscopic observation. Still further, noticeable bluish dark sediment was observed in reaction mixtures with no effective ingredients according to the present invention after standing overnight, while reaction mixtures with any of the effective ingredients according to the present invention remained transparent brown and contained no sedimentation.

(c) Consideration

Formation of melanochromes was suppressed in reaction mixtures containing any of the effective ingredients according to the present invention. This can be explained by the mechanism in which the effective ingredients according to the present invention form chemical complexes with melanin monomers which have been formed from DOPAchrome, thus this melanin monomer trapping inhibits the polymerization of DOPAchrome.

TABLE 1

Inhibition on the formation of melanochrome from DOPAchrome of BPA

| Control | Concentration of BPA (mg/ml) | Absorbance at a wavelength of 500 nm | Macroscopic observation | |
|---|---|---|---|---|
| | | | On measurement | After overnight standing at ambient temperature |
| Control | 0 | 1.19 | Dark Fine sedimentation | Dark Bluish dark sedimentation |
| 1 | 0.25 | 0.80 | Brown | Brown |
| 2 | 0.50 | 0.70 | Brown | Brown |
| 3 | 1.00 | 0.58 | Brown | Brown |
| 4 | 2.50 | 0.43 | Brown | Brown |
| 5 | 5.00 | 0.33 | Brown | Brown |
| 6 | 7.50 | 0.27 | Brown | Brown |
| 7 | 10.00 | 0.24 | Brown | Brown |

TABLE 2

Inhibition on the formation of melanochrome from DOPAchrome of potassium borotartrate

| Control | Concentration of potassium borotartrate (mg/ml) | Absorbance at a wavelength of 500 nm | Macroscopic observation | |
|---|---|---|---|---|
| | | | On measurement | After overnight standing at ambient temperature |
| Control | 0 | 1.245 | Dark Fine sedimentation | Dark Bluish dark-sedimentation |
| 1 | 0.25 | 1.127 | Brown | Brown |
| 2 | 0.50 | 1.119 | Brown | Brown |
| 3 | 1.00 | 1.045 | Brown | Brown |
| 4 | 2.50 | 0.806 | Brown | Brown |
| 5 | 5.00 | 0.635 | Brown | Brown |
| 6 | 7.50 | 0.553 | Brown | Brown |
| 7 | 10.00 | 0.480 | Brown | Brown |

TABLE 3

Inhibition on the formation of melanochrome from DOPAchrome of dihydroxyphenylborane

| Control | Concentration of dihydroxy-phenylborane (mg/ml) | Absorbance at a wavelength of 500 nm | Macroscopic observation | |
|---|---|---|---|---|
| | | | On measurement | After overnight standing at ambient temperature |
| Control | 0 | 1.305 | Dark Fine sedimentation | Dark Bluish dark-sedimentation |
| 1 | 0.25 | 0.924 | Brown | Brown |
| 2 | 0.50 | 0.771 | Brown | Brown |
| 3 | 1.00 | 0.602 | Brown | Brown |
| 4 | 2.50 | 0.381 | Brown | Brown |
| 5 | 5.00 | 0.283 | Brown | Brown |
| 6 | 7.50 | 0.240 | Brown | Brown |
| 7 | 10.00 | 0.172 | Brown | Brown |

TABLE 4

Inhibition on the formation of melanochrome from DOPAchrome of boroglycine

| Control | Concentration of boroglycine (mg/ml) | Absorbance at a wavelength of 500 nm | Macroscopic observation | |
|---|---|---|---|---|
| | | | On measurement | After overnight standing at ambient temperature |
| Control | 0 | 1.144 | Dark Fine sedimentation | Dark Bluish dark-sedimentation |
| 1 | 0.50 | 0.873 | Brown | Brown |
| 2 | 1.00 | 0.817 | Brown | Brown |
| 3 | 2.00 | 0.703 | Brown | Brown |
| 4 | 5.00 | 0.380 | Brown | Brown |
| 5 | 8.00 | 0.217 | Brown | Brown |

TABLE 5

Inhibition on the formation of melanochrome from DOPAchrome of tetrasodium borate

| Control | Concentration of tetrasodium borate (mg/ml) | Absorbance at a wavelength of 500 nm | Macroscopic observation | |
|---|---|---|---|---|
| | | | On measurement | After overnight standing at ambient temperature |
| Control | 0 | 1.269 | Dark Fine sedimentation | Dark Bluish dark-sedimentation |
| 1 | 0.25 | 1.098 | Brown | Brown |
| 2 | 0.50 | 0.988 | Brown | Brown |
| 3 | 1.00 | 0.749 | Brown | Brown |
| 4 | 2.50 | 0.523 | Brown | Brown |
| 5 | 5.00 | 0.329 | Brown | Brown |
| 6 | 7.50 | 0.227 | Brown | Brown |
| 7 | 10.00 | 0.153 | Brown | Brown |

TABLE 6

Inhibition on the formation of melanochrome from DOPAchrome of boric acid

| Control | Concentration of boric acid (mg/ml) | Absorbance at a wavelength of 500 nm | Macroscopic observation | |
|---|---|---|---|---|
| | | | On measurement | After overnight standing at ambient temperature |
| Control | 0 | 1.226 | Dark Fine sedimentation | Dark Bluish dark-sedimentation |
| 1 | 0.25 | 0.955 | Brown | Brown |
| 2 | 0.50 | 0.759 | Brown | Brown |
| 3 | 1.00 | 0.602 | Brown | Brown |
| 4 | 2.50 | 0.417 | Brown | Brown |
| 5 | 5.00 | 0.279 | Brown | Brown |
| 6 | 7.50 | 0.223 | Brown | Brown |
| 7 | 10.00 | 0.172 | Brown | Brown |

Experiment 2

Whitening Effect on Cultured Melanoma Cells (a) Method

Procedure $1 \times 10^5$ cells of B16F10 cells were seeded in commonly used medium which was replaced after 8 hours with those containing either boronophenylalanine, potassium borotartrate, dihydroxyphenylborane, boroglycine, tetrasodium borate and boric acid at respective concentrations given in Tables 7 to 12, followed by cultivation. Cultured medium was changed 3 days after the beginning of cultivation, and 6 days after the cells were collected and subjected to macroscopic observation.

(b) Results

Results are shown in Tables 7 to 12. The B16F10 cells cultured in medium with any of the effective ingredients according to the present invention marked a more noticeable whitening in comparison with those which had been cultured in medium containing no ingredients according to the present invention.

TABLE 7

Skin-whitening effect of BPA on cultured melanoma cells

| | Concentration of BPA ($\mu$g/ml) | Macroscopic observation |
|---|---|---|
| Control | 0 | Unchanged |
| 1 | 500 | Slightly whitened |
| 2 | 1000 | Whitened |

TABLE 8

Skin-whitening effect of borotartaric acid on cultured melanoma cells

| | Concentration of borotartaric acid ($\mu$g/ml) | Macroscopic observation |
|---|---|---|
| Control | 0 | Unchanged |
| 1 | 200 | Slightly whitened |
| 2 | 400 | Whitened |

TABLE 9

Skin-whitening effect of dihydroxyphenylborane on cultured melanoma cells

| | Concentration of dihydroxyphenylborane ($\mu$g/ml) | Macroscopic observation |
|---|---|---|
| Control | 0 | Unchanged |
| 1 | 200 | Slightly whitened |
| 2 | 500 | Whitened |

TABLE 10

Skin-whitening effect of boroglycine on cultured melanoma cells

| | Concentration of boroglycine ($\mu$g/ml) | Macroscopic observation |
|---|---|---|
| Control | 0 | Unchanged |
| 1 | 200 | Slightly whitened |
| 2 | 500 | Whitened |

TABLE 11

Skin-whitening effect of tetrasodium borate on cultured melanoma cells

| | Concentration of tetrasodium borate ($\mu$g/ml) | Macroscopic observation |
|---|---|---|
| Control | 0 | Unchanged |
| 1 | 100 | Slightly whitened |
| 2 | 200 | Whitened |

TABLE 12

Skin-whitening effect of boric acid on cultured melanoma cells

| | Concentration of boric acid ($\mu$g/ml) | Macroscopic observation |
|---|---|---|
| Control | 0 | Unchanged |
| 1 | 200 | Slightly whitened |
| 2 | 400 | Whitened |

Example of Formulations

Following are examples of formulation according to the present invention. In respective formulations, the wording "appropriate" shall refer to the amount of specified ingredient which is to bring the total amounts in respective formulations up to 100% by weight.

Formulation 1

Cream

| Ingredients | Amounts (% by weight) |
|---|---|
| BPA | 1.00 |
| Sodium hyaluronate | 2.00 |
| Polyethylene glycol 400 | 3.00 |
| Polyoxyethylene cetylether (EO 25) | 5.00 |
| Stearic acid | 5.00 |
| Avocado oil | 1.00 |
| Almond oil | 10.00 |
| Sodium dl-pyrrolidonecarboxylate solution | 5.00 |
| Parahydroxybenzoate | 0.70 |
| Disodium edetate | 0.01 |
| Refined water | Appropriate |

Formulation 2

Cream

| Ingredients | Amounts (% by weight) |
|---|---|
| Melanosome | 2.0 |
| Boric acid | 0.5 |
| Polyethyleneglycol monostearate (EO 40) | 2.0 |
| Self-emulsifying glyceryl monostearate | 5.0 |
| Stearic acid | 5.0 |
| Behenyl alcohol | 1.0 |
| Liquid paraffin | 10.0 |
| Glyceryl trioctanoate | 10.0 |
| Glycerine | 5.0 |
| Ethylparaben | 0.1 |
| Refined water | Appropriate |

Formulation 3

Milky lotion

| Ingredients | Amounts (% by weight) |
|---|---|
| Dihydroxyphenylborane | 4.00 |
| 2-Octyldodecanol | 3.00 |
| Polyoxyethylene cetylether (EO 25) | 0.50 |
| Polyoxyethylene oleylether (EO 20) | 1.00 |
| Stearic acid | 0.50 |
| Shea butter | 0.50 |
| Avocado oil | 4.00 |

-continued

Milky lotion

| Ingredients | Amounts (% by weight) |
| --- | --- |
| 4-tert-Butyl-4'-methoxy-dibenzoyl methane | 5.00 |
| Parahydroxybenzoate | 0.20 |
| Quince seed extract | 5.00 |
| Xanthan gum | 0.14 |
| Disodium edetate | 0.01 |
| Refined water | Appropriate |

Formulation 4

Milk

| Ingredients | Amounts (% by weight) |
| --- | --- |
| Tetrasodium borate | 0.50 |
| Glycol salicylate | 0.10 |
| Butylalcohol | 3.50 |
| Arbutin | 2.00 |
| Coconut fatty acid monoethanolamine | 2.00 |
| Stearic acid | 0.50 |
| Myristic acid | 0.50 |
| Avocado oil | 4.00 |
| Octyl methooxycinnamate | 2.00 |
| Natural vitamin E | 0.04 |
| Parahydroxybenzoate | 0.20 |
| Sodium hyaluronate | 5.00 |
| Scutellaria root extract | 0.14 |
| Disodium edetate | 0.01 |
| Refined water | Appropriate |

Formulation 5

Facial lotion

| Ingredients | Amounts (% by weight) |
| --- | --- |
| BPA | 1.00 |
| Boroglycine | 0.25 |
| Ethanol | 15.00 |
| Ethylparaben | 0.10 |
| Citric aid | 0.10 |
| Sodium citrate | 0.30 |
| 1,3-Butylene glycol | 4.00 |
| Disodium edetate | 0.01 |
| Refined water | Appropriate |

Formulation 6

Cream facial pack

| Ingredient | Amounts (% by weight) |
| --- | --- |
| Borodimethylglycine | 3.00 |
| Polyethylene glycol 1500 | 5.00 |
| Stearic acid diethanolamide | 5.00 |
| Stearic acid | 5.00 |
| Myristic | 5.00 |
| Coconut oil | 15.00 |
| Natural vitamin E | 0.04 |
| Parahydroxybenzoate | 0.20 |
| Sodium dl-pyrrolidone carboxylate solution | 5.00 |
| Disodium edetate | 0.01 |
| Refined water | Appropriate |

Formulation 7

Ointment

| Ingredients | Amounts (% by weight) |
| --- | --- |
| Borobetaine | 1.00 |
| Phenyl salicylate | 0.40 |
| Sodium hydroxymethoxybenzophenone sulfonate | 1.00 |
| Isoamyloctyl gallate | 2.00 |
| Coconut fatty acid monoethanolamide | 5.00 |
| Petrolatum | 10.00 |
| Stearic acid | 5.00 |
| Oleic acid | 1.00 |
| Olive oil | 10.00 |
| Parahydroxybenzoate | 0.30 |
| Carrageenan | 5.00 |
| Disodium edetate | 0.01 |
| Refined water | Appropriate |

Formulation 8

Poultice

| Ingredients | Amounts (% by weight) |
| --- | --- |
| Potassium borotartrate | 0.50 |
| Boroglycine | 0.10 |
| Allantoin | 0.10 |
| Stearic acid diethanolamide | 3.00 |
| Polyacrylic acid | 27.00 |
| Ethanolic glycyrrhiza extract | 0.10 |
| Aqueous scutellaria extract | 0.05 |
| Disodium edetate | 0.05 |
| Methoxycinnamate | 4.00 |
| Sodium polyacrylate | 7.00 |
| Aluminum chloride | 0.30 |
| Concentrated glycerin | 20.00 |
| Titanium oxide | 4.00 |
| Refined water | Appropriate |

Formulation 9

Essence

| Ingredients | Amounts (% by weight) |
| --- | --- |
| Lysosome | 1.00 |
| Urocanic acid | 0.50 |
| Isopropanol | 0.50 |
| Benzylalcohol | 0.05 |
| Aqueous keffiran solution | 1.50 |
| Coconut fatty acid monoethanolamide | 2.00 |
| Stearic acid | 0.50 |
| Linolenic acid | 0.50 |
| Avocado oil | 2.00 |
| Turtle oil | 3.00 |
| Natural vitamin E | 0.04 |
| Parahydroxybenzoate | 1.00 |
| One percent of aqueous carboxylvinylpolymer solution | 5.00 |
| Placental extract | 0.14 |
| Disodium edetate | 0.01 |
| Refined water | Appropriate |

It was confirmed that the skin-whitening agents with these formulations exhibited similar efficacies as those shown in the above described Experiments.

The present invention provides a novel skin-whitening agent comprising as its effective ingredient a group of substances which form chemical complexes with melanin monomers. This skin-whitening agent is highly safe for humans and superior in skin-whitening effect.

While there has been described what is at present considered to be the preferred embodiments of the invention, it will be understood the various modifications may be made therein, and it is intended to cover in the appended claims all such modifications as fall within the true spirit and scope of the invention.

What we claim is:

1. A skin-whitening composition which comprises a carrier and, as its effective ingredient, a substance which bears the property of forming chemical complexes with melanin monomers.

2. The skin-whitening composition of claim 1, wherein the substance is boron-containing compound and/or natural substances originated from an animal, a plant or a microorganism.

3. The skin-whitening composition of claim 2, wherein the boron-containing compound is one or more members selected from the group consisting of boronophenylalanine, borophenolic acid derivatives boroglycine, borodimethylglycine, potassium borotartrate, boric acid, dihydroxyphenylborane, borobetaine, and tetrasodium borate.

4. A skin-whitening agent which comprises as its effective ingredient a natural substance which is an extract of coated vesicles, melanosomes, lysosomes, and/or organelles originated from an animal, a plant or a microorganism.

* * * * *